United States Patent
Duke

(10) Patent No.: US 8,690,831 B2
(45) Date of Patent: Apr. 8, 2014

(54) GAS JET FLUID REMOVAL IN A TROCAR

(75) Inventor: Daniel H. Duke, West Chester, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 802 days.

(21) Appl. No.: 12/109,881

(22) Filed: Apr. 25, 2008

(65) Prior Publication Data

US 2009/0270818 A1  Oct. 29, 2009

(51) Int. Cl.
 *A61M 5/178* (2006.01)
 *A61M 37/00* (2006.01)
 *A61M 25/00* (2006.01)

(52) U.S. Cl.
 USPC .............. 604/164.01; 604/23; 604/167.01; 604/264; 604/167.06

(58) Field of Classification Search
 USPC ........ 604/27, 167.03–167.04, 274, 264, 506, 604/167.01–167.02, 165.01, 167.06, 23, 604/164.01; 606/185; 608/108–109
 See application file for complete search history.

(56) References Cited

U.S. PATENT DOCUMENTS

| | | |
|---|---|---|
| 3,900,022 A | 8/1975 | Widran |
| 3,903,877 A | 9/1975 | Terada et al. |
| 3,924,608 A | 12/1975 | Mitsui et al. |
| 3,980,078 A | 9/1976 | Tominaga et al. |
| 3,981,276 A | 9/1976 | Ernest |
| 4,204,563 A | 5/1980 | Pyle |
| 4,279,246 A | 7/1981 | Chikama et al. |
| 4,687,033 A | 8/1987 | Furrow et al. |
| 4,690,140 A | 9/1987 | Mecca |
| 4,722,000 A | 1/1988 | Chatenever |
| 4,836,187 A | 6/1989 | Iwakoshi et al. |
| 4,874,364 A | 10/1989 | Morris et al. |
| 4,877,016 A | 10/1989 | Kantor et al. |
| 4,919,305 A | 4/1990 | Podgers |

(Continued)

FOREIGN PATENT DOCUMENTS

| | | |
|---|---|---|
| CA | 2060930 | 10/1992 |
| CA | 2661238 A1 | 10/2009 |

(Continued)

OTHER PUBLICATIONS

U.S. Appl. No. 11/771,263 for "Duckbill Seal with Fluid Drainage Feature," filed Jun. 29, 2007, Paul Franer et al.

(Continued)

*Primary Examiner* — Bhisma Mehta
*Assistant Examiner* — Bradley G Thomas, Jr.
(74) *Attorney, Agent, or Firm* — Nutter McClennen & Fish LLP

(57) ABSTRACT

Devices and methods are provided for removing fluid from a surgical access device and/or from surgical instruments passed therethrough, and for preventing such fluid from accumulating. For example, in one embodiment, an exemplary device can include a body defining a working channel that is configured and sized to allow for passage of a surgical instrument therethrough. A number of seals can be disposed in the working channel so as to contact the inserted surgical instrument. One or more outlets can be oriented to direct gas, such as air or an insufflation gas, into the working channel so as to remove fluid on the seals, or other parts of the surgical access device, as well as the surgical instruments themselves. In some embodiments, constant flows of gases can be arranged to act as shields to help prevent fluid from accumulating on the surgical access device and/or surgical instruments.

15 Claims, 12 Drawing Sheets

(56) References Cited

U.S. PATENT DOCUMENTS

| | | |
|---|---|---|
| 4,943,280 A | 7/1990 | Lander |
| 5,084,057 A | 1/1992 | Green et al. |
| 5,104,383 A | 4/1992 | Shichman |
| 5,112,308 A | 5/1992 | Olsen et al. |
| 5,127,909 A | 7/1992 | Shichman |
| 5,167,220 A | 12/1992 | Brown |
| 5,180,373 A | 1/1993 | Green et al. |
| 5,191,878 A | 3/1993 | Iida et al. |
| 5,197,955 A | 3/1993 | Stephens et al. |
| 5,201,714 A | 4/1993 | Gentelia et al. |
| 5,207,213 A | 5/1993 | Auhll et al. |
| 5,209,737 A | 5/1993 | Ritchart et al. |
| 5,226,891 A | 7/1993 | Bushatz et al. |
| 5,237,984 A | 8/1993 | Williams, III et al. |
| 5,279,542 A | 1/1994 | Wilk |
| 5,312,351 A | 5/1994 | Gerrone |
| 5,312,363 A | 5/1994 | Ryan et al. |
| 5,312,397 A | 5/1994 | Cosmescu |
| 5,313,934 A | 5/1994 | Wiita et al. |
| 5,320,608 A | 6/1994 | Gerrone |
| 5,320,610 A | 6/1994 | Yoon |
| 5,326,013 A | 7/1994 | Green et al. |
| 5,330,437 A | 7/1994 | Durman |
| 5,334,164 A | 8/1994 | Guy et al. |
| 5,337,730 A | 8/1994 | Maguire |
| 5,339,800 A | 8/1994 | Wiita et al. |
| 5,342,315 A | 8/1994 | Rowe et al. |
| 5,347,988 A | 9/1994 | Hori |
| 5,350,364 A | 9/1994 | Stephens et al. |
| 5,354,302 A | 10/1994 | Ko |
| 5,364,002 A | 11/1994 | Green et al. |
| 5,369,525 A | 11/1994 | Bala et al. |
| 5,382,297 A | 1/1995 | Valentine et al. |
| 5,389,081 A | 2/1995 | Castro |
| 5,391,154 A | 2/1995 | Young |
| 5,392,766 A | 2/1995 | Masterson et al. |
| 5,395,342 A | 3/1995 | Yoon |
| 5,400,767 A | 3/1995 | Murdoch et al. |
| 5,419,309 A | 5/1995 | Biehl |
| 5,441,513 A | 8/1995 | Roth |
| 5,443,452 A | 8/1995 | Hart et al. |
| 5,448,990 A | 9/1995 | De Faria-Correa et al. |
| 5,449,370 A | 9/1995 | Vaitekunas |
| 5,458,633 A | 10/1995 | Bailey |
| 5,458,640 A | 10/1995 | Gerrone |
| 5,462,100 A | 10/1995 | Covert et al. |
| 5,464,008 A | 11/1995 | Kim |
| 5,476,475 A | 12/1995 | Gadberry |
| 5,486,154 A | 1/1996 | Kelleher |
| 5,492,304 A | 2/1996 | Smith et al. |
| 5,496,280 A | 3/1996 | Vandenbroek et al. |
| 5,496,345 A | 3/1996 | Kieturakis et al. |
| 5,496,411 A | 3/1996 | Candy et al. |
| 5,514,084 A | 5/1996 | Fisher |
| 5,514,153 A | 5/1996 | Bonutti |
| 5,518,026 A | 5/1996 | Benjey |
| 5,518,502 A | 5/1996 | Kaplan et al. |
| 5,533,496 A | 7/1996 | De Faria-Correa et al. |
| 5,535,759 A | 7/1996 | Wilk |
| 5,536,234 A | 7/1996 | Newman |
| 5,542,931 A | 8/1996 | Gravener et al. |
| 5,545,142 A | 8/1996 | Stephens et al. |
| 5,545,179 A | 8/1996 | Williamson, IV |
| 5,549,543 A | 8/1996 | Kim |
| 5,551,448 A | 9/1996 | Matula et al. |
| 5,554,151 A | 9/1996 | Hinchliffe |
| 5,568,828 A | 10/1996 | Harris |
| 5,569,183 A | 10/1996 | Kieturakis |
| 5,569,205 A | 10/1996 | Hart et al. |
| 5,575,756 A | 11/1996 | Karasawa et al. |
| 5,584,850 A | 12/1996 | Hart et al. |
| 5,590,697 A | 1/1997 | Benjey et al. |
| 5,603,702 A | 2/1997 | Smith et al. |
| 5,605,175 A | 2/1997 | Bergsma et al. |
| 5,628,732 A | 5/1997 | Antoon, Jr. et al. |
| 5,630,795 A | 5/1997 | Kuramoto et al. |
| 5,634,911 A | 6/1997 | Hermann et al. |
| 5,643,227 A | 7/1997 | Stevens |
| 5,643,301 A | 7/1997 | Mollenauer |
| 5,647,372 A | 7/1997 | Tovey et al. |
| 5,647,840 A | 7/1997 | D'Amelio et al. |
| 5,651,757 A | 7/1997 | Meckstroth |
| 5,658,273 A | 8/1997 | Long |
| 5,662,614 A | 9/1997 | Edoga |
| 5,685,823 A | 11/1997 | Ito et al. |
| 5,688,222 A | 11/1997 | Hluchy et al. |
| 5,709,664 A | 1/1998 | Vandenbroek et al. |
| 5,720,756 A | 2/1998 | Green et al. |
| 5,720,759 A | 2/1998 | Green et al. |
| 5,725,477 A | 3/1998 | Yasui et al. |
| 5,725,478 A | 3/1998 | Saad |
| 5,743,884 A | 4/1998 | Hasson et al. |
| 5,752,938 A | 5/1998 | Flatland et al. |
| 5,755,252 A | 5/1998 | Bergsma et al. |
| 5,755,732 A | 5/1998 | Green et al. |
| 5,782,859 A | 7/1998 | Nicholas et al. |
| 5,788,676 A | 8/1998 | Yoon |
| 5,792,044 A | 8/1998 | Foley et al. |
| 5,792,113 A | 8/1998 | Kramer et al. |
| 5,797,434 A | 8/1998 | Benjey et al. |
| 5,807,338 A | 9/1998 | Smith et al. |
| 5,814,026 A | 9/1998 | Yoon |
| 5,817,061 A | 10/1998 | Goodwin et al. |
| 5,848,992 A | 12/1998 | Hart et al. |
| 5,860,458 A | 1/1999 | Benjey et al. |
| 5,871,440 A | 2/1999 | Okada et al. |
| 5,882,345 A | 3/1999 | Yoon |
| 5,902,231 A | 5/1999 | Foley et al. |
| 5,902,264 A | 5/1999 | Toso et al. |
| 5,906,595 A | 5/1999 | Powell et al. |
| 5,954,635 A | 9/1999 | Foley et al. |
| 5,957,888 A | 9/1999 | Hinchliffe |
| 5,964,781 A | 10/1999 | Mollenauer et al. |
| 5,983,958 A | 11/1999 | Bergsma et al. |
| 5,989,224 A | 11/1999 | Exline et al. |
| 6,004,326 A | 12/1999 | Castro et al. |
| 6,007,487 A | 12/1999 | Foley et al. |
| 6,017,333 A | 1/2000 | Bailey |
| 6,062,276 A | 5/2000 | Benjey et al. |
| 6,063,050 A | 5/2000 | Manna et al. |
| 6,110,103 A | 8/2000 | Donofrio |
| 6,126,592 A | 10/2000 | Proch et al. |
| 6,152,871 A | 11/2000 | Foley et al. |
| 6,159,182 A | 12/2000 | Davis et al. |
| 6,162,170 A | 12/2000 | Foley et al. |
| 6,167,920 B1 | 1/2001 | Enge |
| 6,176,823 B1 | 1/2001 | Foley et al. |
| 6,176,825 B1 | 1/2001 | Chin et al. |
| 6,206,057 B1 | 3/2001 | Benjey et al. |
| 6,206,822 B1 | 3/2001 | Foley et al. |
| 6,216,661 B1 | 4/2001 | Pickens et al. |
| 6,217,509 B1 | 4/2001 | Foley et al. |
| 6,253,802 B1 | 7/2001 | Enge |
| 6,258,065 B1 | 7/2001 | Dennis et al. |
| 6,264,604 B1 | 7/2001 | Kieturakis et al. |
| 6,287,313 B1 | 9/2001 | Sasso |
| 6,354,992 B1 | 3/2002 | Kato |
| 6,371,909 B1 | 4/2002 | Hoeg et al. |
| 6,409,657 B1 | 6/2002 | Kawano et al. |
| 6,423,266 B1 | 7/2002 | Choperena et al. |
| 6,425,535 B1 | 7/2002 | Akiba et al. |
| 6,425,859 B1 | 7/2002 | Foley et al. |
| 6,443,190 B1 | 9/2002 | Enge |
| 6,447,446 B1 | 9/2002 | Smith et al. |
| 6,482,181 B1 | 11/2002 | Racenet et al. |
| 6,494,893 B2 | 12/2002 | Dubrul et al. |
| 6,497,687 B1 | 12/2002 | Blanco |
| 6,516,835 B2 | 2/2003 | Enge |
| 6,520,907 B1 | 2/2003 | Foley et al. |
| 6,534,002 B1 | 3/2003 | Lin et al. |
| 6,551,282 B1 | 4/2003 | Exline et al. |
| 6,562,046 B2 | 5/2003 | Sasso |
| 6,569,120 B1 | 5/2003 | Green et al. |
| 6,595,915 B2 | 7/2003 | Akiba et al. |

(56) References Cited

U.S. PATENT DOCUMENTS

| | | |
|---|---|---|
| 6,595,946 B1 | 7/2003 | Pasqualucci |
| 6,601,617 B2 | 8/2003 | Enge |
| 6,605,098 B2 | 8/2003 | Nobis et al. |
| 6,638,214 B2 | 10/2003 | Akiba et al. |
| 6,648,906 B2 | 11/2003 | Lasheras et al. |
| 6,679,833 B2 | 1/2004 | Smith et al. |
| 6,679,834 B2 | 1/2004 | Stahl et al. |
| 6,679,837 B2 | 1/2004 | Daikuzono |
| 6,685,665 B2 * | 2/2004 | Booth et al. ............... 604/26 |
| 6,699,185 B2 | 3/2004 | Gminder et al. |
| 6,702,787 B2 | 3/2004 | Racenet et al. |
| 6,712,757 B2 | 3/2004 | Becker et al. |
| 6,726,663 B1 | 4/2004 | Dennis |
| 6,755,782 B2 | 6/2004 | Ogawa et al. |
| 6,860,869 B2 | 3/2005 | Dennis |
| 6,860,892 B1 | 3/2005 | Tanaka et al. |
| 6,918,924 B2 | 7/2005 | Lasheras et al. |
| 6,923,759 B2 | 8/2005 | Kasahara et al. |
| 6,942,671 B1 | 9/2005 | Smith |
| 6,981,966 B2 | 1/2006 | Green et al. |
| 6,989,003 B2 | 1/2006 | Wing et al. |
| 7,008,416 B2 | 3/2006 | Sakaguchi et al. |
| 7,025,747 B2 | 4/2006 | Smith |
| 7,052,454 B2 | 5/2006 | Taylor |
| 7,056,303 B2 | 6/2006 | Dennis et al. |
| 7,056,321 B2 | 6/2006 | Pagliuca et al. |
| 7,077,803 B2 | 7/2006 | Kasahara et al. |
| 7,083,626 B2 | 8/2006 | Hart et al. |
| 7,104,657 B2 | 9/2006 | Sherwin et al. |
| 7,105,009 B2 | 9/2006 | Johnson et al. |
| 7,112,185 B2 | 9/2006 | Hart et al. |
| 7,163,525 B2 | 1/2007 | Franer |
| 7,169,130 B2 | 1/2007 | Exline et al. |
| 7,198,598 B2 | 4/2007 | Smith et al. |
| 7,207,347 B2 | 4/2007 | Olshanetsky et al. |
| 7,244,244 B2 | 7/2007 | Racenet et al. |
| 7,344,519 B2 | 3/2008 | Wing et al. |
| 7,473,243 B2 | 1/2009 | Dennis et al. |
| 7,591,802 B2 | 9/2009 | Johnson et al. |
| 2002/0022762 A1 | 2/2002 | Beane et al. |
| 2002/0065450 A1 | 5/2002 | Ogawa |
| 2002/0068923 A1 | 6/2002 | Caldwell et al. |
| 2002/0103420 A1 | 8/2002 | Coleman et al. |
| 2002/0107484 A1 | 8/2002 | Dennis et al. |
| 2002/0161387 A1 | 10/2002 | Blanco |
| 2003/0004529 A1 | 1/2003 | Tsonton et al. |
| 2003/0060770 A1 | 3/2003 | Wing et al. |
| 2003/0130674 A1 | 7/2003 | Kasahara et al. |
| 2003/0139756 A1 | 7/2003 | Brustad |
| 2003/0195472 A1 | 10/2003 | Green et al. |
| 2004/0034339 A1 | 2/2004 | Stoller et al. |
| 2004/0106942 A1 | 6/2004 | Taylor et al. |
| 2004/0111052 A1 * | 6/2004 | Moenning ............... 604/26 |
| 2004/0167559 A1 | 8/2004 | Taylor et al. |
| 2004/0171990 A1 | 9/2004 | Dennis et al. |
| 2004/0220452 A1 | 11/2004 | Shalman |
| 2004/0230161 A1 * | 11/2004 | Zeiner ............... 604/167.06 |
| 2004/0256004 A1 | 12/2004 | Kessell et al. |
| 2004/0260244 A1 | 12/2004 | Piechowicz et al. |
| 2005/0015043 A1 * | 1/2005 | Stubbs et al. ............ 604/26 |
| 2005/0033342 A1 | 2/2005 | Hart et al. |
| 2005/0043683 A1 | 2/2005 | Ravo |
| 2005/0059865 A1 | 3/2005 | Kahle et al. |
| 2005/0059934 A1 | 3/2005 | Wenchell et al. |
| 2005/0070850 A1 | 3/2005 | Albrecht |
| 2005/0070946 A1 | 3/2005 | Franer et al. |
| 2005/0070947 A1 | 3/2005 | Franer et al. |
| 2005/0077688 A1 * | 4/2005 | Voegele et al. ............ 277/628 |
| 2005/0077689 A1 | 4/2005 | Hueil |
| 2005/0096605 A1 | 5/2005 | Green et al. |
| 2005/0131349 A1 | 6/2005 | Albrecht et al. |
| 2005/0203543 A1 | 9/2005 | Hilal et al. |
| 2005/0216028 A1 | 9/2005 | Hart et al. |
| 2005/0241647 A1 | 11/2005 | Nguyen et al. |
| 2005/0288622 A1 | 12/2005 | Albrecht et al. |
| 2006/0020165 A1 | 1/2006 | Adams |
| 2006/0047240 A1 | 3/2006 | Kumar et al. |
| 2006/0052666 A1 | 3/2006 | Kumar et al. |
| 2006/0068360 A1 | 3/2006 | Boulais |
| 2006/0069312 A1 | 3/2006 | O'Connor |
| 2006/0100485 A1 | 5/2006 | Arai et al. |
| 2006/0122556 A1 | 6/2006 | Kumar et al. |
| 2006/0122557 A1 | 6/2006 | Kumar et al. |
| 2006/0129098 A1 | 6/2006 | Hart et al. |
| 2006/0135972 A1 | 6/2006 | Zeiner |
| 2006/0135977 A1 | 6/2006 | Thompson et al. |
| 2006/0135978 A1 | 6/2006 | Franer |
| 2006/0149137 A1 | 7/2006 | Pingleton et al. |
| 2006/0199998 A1 | 9/2006 | Akui et al. |
| 2006/0211916 A1 | 9/2006 | Kasahara et al. |
| 2006/0224121 A1 | 10/2006 | Hart et al. |
| 2006/0224164 A1 | 10/2006 | Hart et al. |
| 2006/0229565 A1 | 10/2006 | Dennis et al. |
| 2006/0235455 A1 | 10/2006 | Oshida |
| 2006/0276688 A1 | 12/2006 | Surti |
| 2006/0293559 A1 | 12/2006 | Grice et al. |
| 2007/0005087 A1 | 1/2007 | Smith et al. |
| 2007/0021713 A1 | 1/2007 | Kumar et al. |
| 2007/0027453 A1 | 2/2007 | Hart et al. |
| 2007/0088275 A1 * | 4/2007 | Stearns et al. .......... 604/164.01 |
| 2007/0088277 A1 | 4/2007 | McGinley et al. |
| 2007/0129719 A1 | 6/2007 | Kendale et al. |
| 2007/0142709 A1 | 6/2007 | Martone et al. |
| 2007/0149931 A1 | 6/2007 | Cannon et al. |
| 2007/0149993 A1 | 6/2007 | Kasahara et al. |
| 2007/0185453 A1 | 8/2007 | Michael et al. |
| 2007/0191759 A1 | 8/2007 | Stoller et al. |
| 2007/0204890 A1 | 9/2007 | Torii |
| 2007/0225566 A1 | 9/2007 | Kawanishi |
| 2007/0244361 A1 | 10/2007 | Ikeda et al. |
| 2008/0009797 A1 | 1/2008 | Stellon et al. |
| 2008/0249475 A1 | 10/2008 | Albrecht et al. |
| 2008/0269696 A1 | 10/2008 | Exline et al. |
| 2009/0005799 A1 | 1/2009 | Franer et al. |
| 2009/0030375 A1 | 1/2009 | Franer et al. |
| 2009/0076456 A1 | 3/2009 | Armstrong et al. |
| 2009/0093682 A1 | 4/2009 | Izzo et al. |
| 2009/0137943 A1 | 5/2009 | Stearns et al. |
| 2009/0149813 A1 | 6/2009 | Franer et al. |
| 2009/0192444 A1 | 7/2009 | Albrecht et al. |
| 2009/0221960 A1 | 9/2009 | Albrecht et al. |
| 2009/0234293 A1 | 9/2009 | Albrecht et al. |
| 2009/0240204 A1 | 9/2009 | Taylor et al. |
| 2009/0264703 A1 | 10/2009 | Pribanic |
| 2009/0270681 A1 | 10/2009 | Moreno et al. |
| 2009/0270685 A1 | 10/2009 | Moreno et al. |
| 2009/0270813 A1 | 10/2009 | Moreno, Jr. et al. |
| 2009/0270817 A1 | 10/2009 | Moreno et al. |
| 2009/0281478 A1 | 11/2009 | Duke |
| 2009/0314422 A1 | 12/2009 | Racenet et al. |
| 2010/0022958 A1 | 1/2010 | Moreno, Jr. et al. |

FOREIGN PATENT DOCUMENTS

| | | |
|---|---|---|
| DE | 19619065 A1 | 11/1997 |
| DE | 10330518 A1 | 2/2005 |
| EP | 0517248 | 12/1992 |
| EP | 0567142 | 10/1993 |
| EP | 568383 A1 | 11/1993 |
| EP | 570802 A1 | 11/1993 |
| EP | 664101 A1 | 7/1995 |
| EP | 0696459 | 2/1996 |
| EP | 731718 B1 | 9/1996 |
| EP | 845960 B1 | 6/1998 |
| EP | 875256 B1 | 11/1998 |
| EP | 890342 B1 | 1/1999 |
| EP | 898971 B1 | 3/1999 |
| EP | 0972493 | 1/2000 |
| EP | 1210904 B1 | 6/2002 |
| EP | 1284664 | 2/2003 |
| EP | 1312318 B1 | 5/2003 |
| EP | 1323373 A3 | 7/2003 |
| EP | 1348386 | 10/2003 |
| EP | 1459688 | 9/2004 |

(56) References Cited

FOREIGN PATENT DOCUMENTS

| | | | |
|---|---|---|---|
| EP | 1629787 | A2 | 3/2006 |
| EP | 1679043 | | 7/2006 |
| EP | 1698291 | | 9/2006 |
| EP | 1707133 | | 10/2006 |
| EP | 1709918 | | 10/2006 |
| EP | 1834571 | A1 | 9/2007 |
| EP | 1834573 | A1 | 9/2007 |
| FR | 2900562 | A1 | 11/2007 |
| GB | 2298906 | A | 9/1996 |
| JP | 61036718 | A2 | 2/1986 |
| JP | 3106329 | A2 | 5/1991 |
| JP | 4020324 | A2 | 1/1992 |
| JP | 4158825 | A2 | 6/1992 |
| JP | 4170929 | A2 | 6/1992 |
| JP | 4329510 | A2 | 11/1992 |
| JP | 5192294 | A2 | 8/1993 |
| JP | 5199979 | A2 | 8/1993 |
| JP | 5207962 | A2 | 8/1993 |
| JP | 6133927 | A2 | 5/1994 |
| JP | 6169879 | A2 | 6/1994 |
| JP | 6304121 | A2 | 11/1994 |
| JP | 7178039 | A2 | 7/1995 |
| JP | 7246187 | A2 | 9/1995 |
| JP | 7289501 | A2 | 11/1995 |
| JP | 7313442 | A2 | 12/1995 |
| JP | 8154888 | A2 | 6/1996 |
| JP | 8173372 | A2 | 7/1996 |
| JP | 10043128 | A2 | 2/1998 |
| JP | 11146882 | A2 | 6/1999 |
| JP | 2002224014 | B2 | 8/2002 |
| JP | 2002238906 | A2 | 8/2002 |
| JP | 2003284686 | A2 | 10/2003 |
| JP | 2004016455 | A2 | 1/2004 |
| JP | 2004267583 | A2 | 9/2004 |
| JP | 2005253543 | A2 | 9/2005 |
| JP | 2005319101 | A2 | 11/2005 |
| JP | 2009261923 | A | 11/2009 |
| WO | WO-9407552 | | 4/1994 |
| WO | 9532012 | A1 | 11/1995 |
| WO | 9532019 | A1 | 11/1995 |
| WO | WO-9604946 | A1 | 2/1996 |
| WO | WO-9740759 | A1 | 11/1997 |
| WO | 9809673 | A1 | 3/1998 |
| WO | WO-0189371 | A1 | 11/2001 |
| WO | WO-02078527 | A2 | 10/2002 |
| WO | WO-02096307 | A2 | 12/2002 |
| WO | WO-03011154 | A2 | 2/2003 |
| WO | WO-2004043275 | A1 | 5/2004 |
| WO | WO-2005016133 | A1 | 2/2005 |
| WO | 2005020293 | A2 | 3/2005 |
| WO | WO-2005097019 | A2 | 10/2005 |
| WO | WO-2005097234 | A2 | 10/2005 |

OTHER PUBLICATIONS

European Search Report for EP 09251178 dated May 21, 2010, pp. 1-5.

* cited by examiner

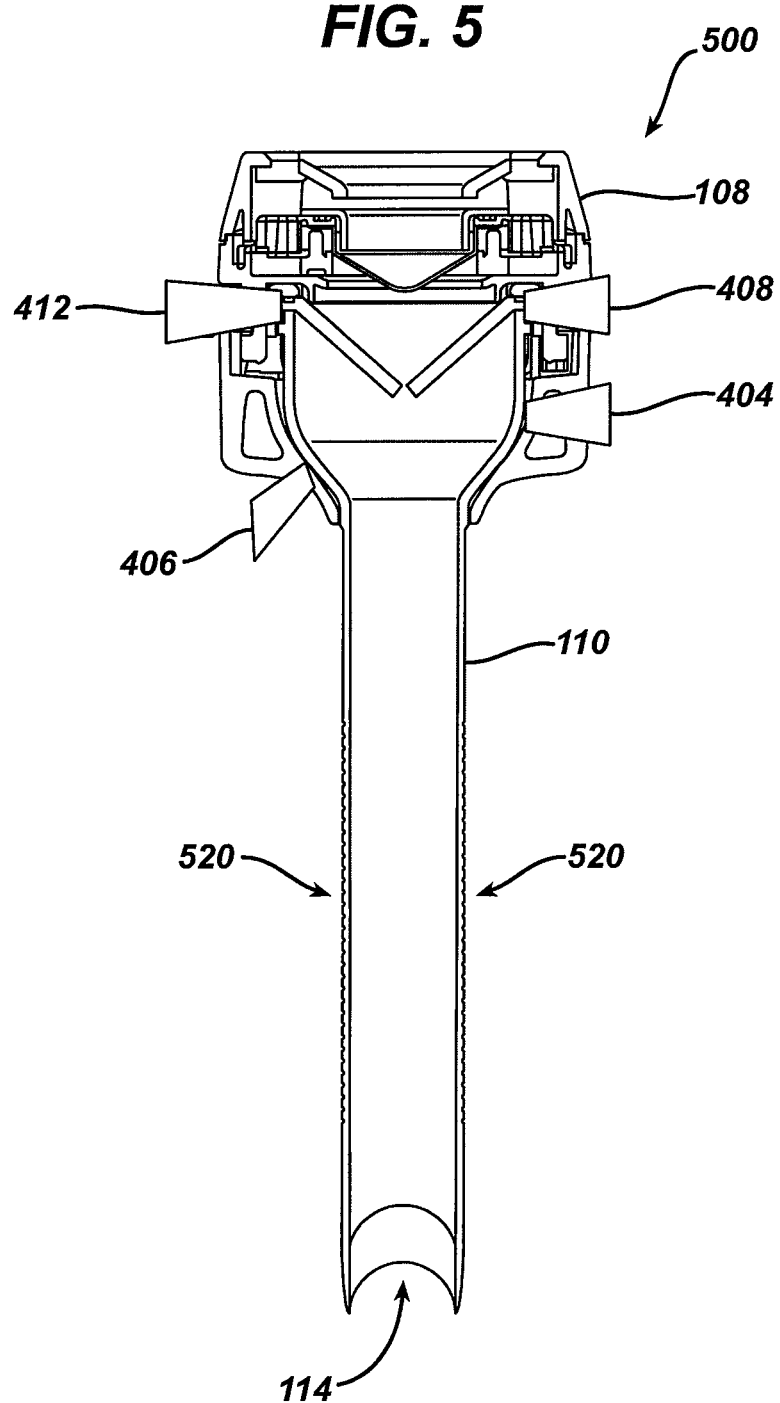

GAS JET FLUID REMOVAL IN A TROCAR

FIELD

The present disclosure generally relates to devices and methods for removing fluids from a surgical access device and/or from surgical instruments passed therethrough and to devices and methods for preventing such fluids from accumulating.

BACKGROUND

During laparoscopic surgery, one or more small incisions are formed in the abdomen and a trocar is inserted through the incision to form a pathway that provides access to the abdominal cavity. The trocar is used to introduce various instruments and tools into the abdominal cavity, as well as to provide insufflation to elevate the abdominal wall above the organs. During such procedures, a scoping device, such as an endoscope or laparoscope, is inserted through one of the trocars to allow a surgeon to view the operative field on an external monitor coupled to the scoping device.

Scoping devices are often inserted and removed through a trocar multiple times during a single surgical procedure, and during each insertion and each removal they can encounter fluid that can adhere to the scopes lens and fully or partially impede visibility through the lens. Furthermore, a scope can draw fluid from inside or outside a patient's body into the trocar and deposit it there. Such fluid can adhere to the lens of the scope or other instrument upon its reinsertion through the trocar. The lens of the scope thus needs to be cleaned to restore visibility, often multiple times during a single surgical procedure. Each lens cleaning can require removing the scope from the body, cleaning fluid from the scope lens, and reintroducing the scope into the body. Such lens cleaning is a time-consuming procedure and can increase the chances of complications and contamination from repeated scope insertion and removal.

Accordingly, there is a need for methods and devices for improving visibility through a lens of a scoping device during a surgical procedure.

SUMMARY

In one embodiment, a surgical access device is provided which includes a body that defines a working channel. The working channel can be configured and sized to allow for passage of a surgical instrument therethrough. The surgical access device also can include a seal extending at least partially across the working channel so as to contact a surgical instrument inserted therethrough and at least one outlet formed through a sidewall of the body. The at least one outlet can be configured to receive gas flow and can be oriented to direct gas flow towards the seal in the working channel for removing fluid on the seal. In some embodiments, the at least one outlet can have tapered nozzles formed thereon.

The body can have a variety of configurations. For example, the body can have proximal and distal ends, and the at least one outlet can be disposed proximal to the seal. The body can include a proximal housing and a distal cannula extending from the housing and configured to be inserted into a body cavity. In some embodiments, the at least one seal and the at least one outlet can be disposed in the proximal housing.

Virtually any kind of seal can be used. For example, the seal can be at least one of a multi-layer seal, a duckbill seal, a flapper seal, an annular seal, a zero-closure seal, a seal with a slit-shaped opening, a universal seal, an O-ring, a diaphragm seal, a gel seal, and so on. The seal can have an opening formed therein and the at least one outlet can be oriented so as to direct gas toward the opening. Further, the seal can have a slit-shaped opening formed therein, and the at least one outlet can be configured to direct gas in a direction substantially perpendicular or parallel to the opening.

The surgical access device can have a wide variety of further features. For example, the surgical access device can include at least one outlet formed through a sidewall of the body and configured to receive gas flow from an insufflation port and deliver gas flow to the working channel. The surgical access device can include a valve element associated with the at least one outlet to control gas flow therethrough. The valve element can be coupled to a control device that provides signals to control gas flow through the valve element. The surgical access device can further include a plurality of outlets, and gas flow from each the plurality of outlets can be independently controllable. The surgical access device can further include an exhaust port coupled to at least one of the working channel and the at least one outlet.

In another embodiment, a trocar assembly is provided which has a housing defining a working channel sized and configured to receive a surgical instrument. In some embodiments, a cannula can extend from the housing, the housing and cannula defining the working channel sized and configured to receive a surgical instrument. The trocar assembly can include a seal disposed in the housing and extending at least partially across the working channel for contacting a surgical instrument. A wide variety of seals can be used, such as a multi-layer seal, a duckbill seal, a flapper seal, an annular seal, a zero-closure seal, a seal with a slit-shaped opening, a universal seal, an O-ring, a diaphragm seal, a gel seal, or others. The trocar assembly also can include at least one inlet formed in the housing for receiving gas and at least one outlet within the working channel and in communication with the at least one inlet. The outlet(s) can be oriented to direct gas flow from the at least one inlet towards the seal. The outlet(s) also can be oriented to direct gas toward an opening formed in the seal. Furthermore, in some embodiments, the working channel of the trocar assembly can have proximal and distal ends, and the at least one outlet can be disposed proximal to the seal.

The trocar assembly can have a wide variety of further features. For example, in some embodiments, the trocar assembly can include at least one outlet within the working channel and configured to receive gas flow from an insufflation port and deliver gas flow to the working channel. In some embodiments, the trocar assembly can include a plurality of outlets, and gas flow from each of the plurality of outlets can be independently controllable. The trocar assembly also can include a valve element associated with the at least one outlet to control gas flow therethrough. The valve element can be coupled to a control device that provides signals to control gas flow through the valve element. The trocar assembly can include an exhaust port coupled to at least one of the working channel, the at least one outlet, and the at least one inlet. A valve element can be associated with the exhaust port and calibrated to release gas therefrom at a predetermined pressure.

Further, the trocar assembly can include a second seal that is disposed in the housing and that has a different shape than the other seal. The second seal can be spaced apart from the other seal and extend at least partially across the working channel. The trocar assembly can further include at least one outlet within the working channel and in communication with the at least one inlet, and the outlet(s) can be oriented to direct gas from the at least one inlet towards the second seal.

In yet another aspect, a method for delivering a surgical instrument to a treatment site is provided. In one embodiment, the method can include passing a surgical instrument through a working channel of a trocar assembly such that at least one seal disposed in the working channel contacts the surgical instrument, and directing gas toward the at least one seal to remove fluid from the at least one seal.

Gases can be directed in a variety of ways. For example, gas can be directed through an outlet that opens into the working channel. A stream of gas can be aimed at the at least one seal. Gas can be directed across an opening formed in the at least one seal. Gas can be directed against the least one seal during passage of the surgical instrument through the working channel.

A wide range of variations are possible. For example, an inlet on the trocar assembly can be coupled to a gas source. The rate of gas flow can be controlled. Further, gas can be released from the working channel via an exhaust path.

In yet another embodiment, a method of processing a device can be provided, and can include obtaining a surgical access device or a trocar assembly, sterilizing the obtained trocar assembly or surgical access device; and storing the trocar assembly or surgical access device in a sterile container.

BRIEF DESCRIPTION OF THE DRAWINGS

The invention will be more fully understood from the following detailed description taken in conjunction with the accompanying drawings, in which:

FIG. 5 is a sectioned side view of an alternate embodiment of a surgical access device which includes a plurality of exemplary inlets formed in the surgical access device and coupled to outlets for directing gas flow toward seals in a working channel;

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present application is defined solely by the claims. The features illustrated or described in connection with one exemplary embodiment may be combined with the features of other embodiments. Such modifications and variations are intended to be included within the scope of the present disclosure.

The present disclosure generally describes methods and devices useful for removing fluid from surgical access devices and/or instruments received therein. They are also useful for preventing fluid from attaching to or accumulating on surgical access devices and/or surgical instruments. They are also useful for removing fluids from instruments, such as scopes, as they pass through surgical access devices, which can be advantageous in controlling and/or limiting the opportunity for such fluids to come in contact with seals or other parts of the surgical access device. A person skilled in the art should appreciate that the term fluid, as used herein, is intended to include any substance that, when on a surgical instrument, can adversely affect the functioning of the instrument or a surgeon's ability to use it. Fluids include any kind of bodily fluid, such as blood, and any kind of fluid introduced during a surgical procedure, such as saline. Fluids also include fluid/solid mixtures or fluids with particles (such as pieces of tissue) suspended or located therein, as well as gases and viscous materials.

Figure 1:
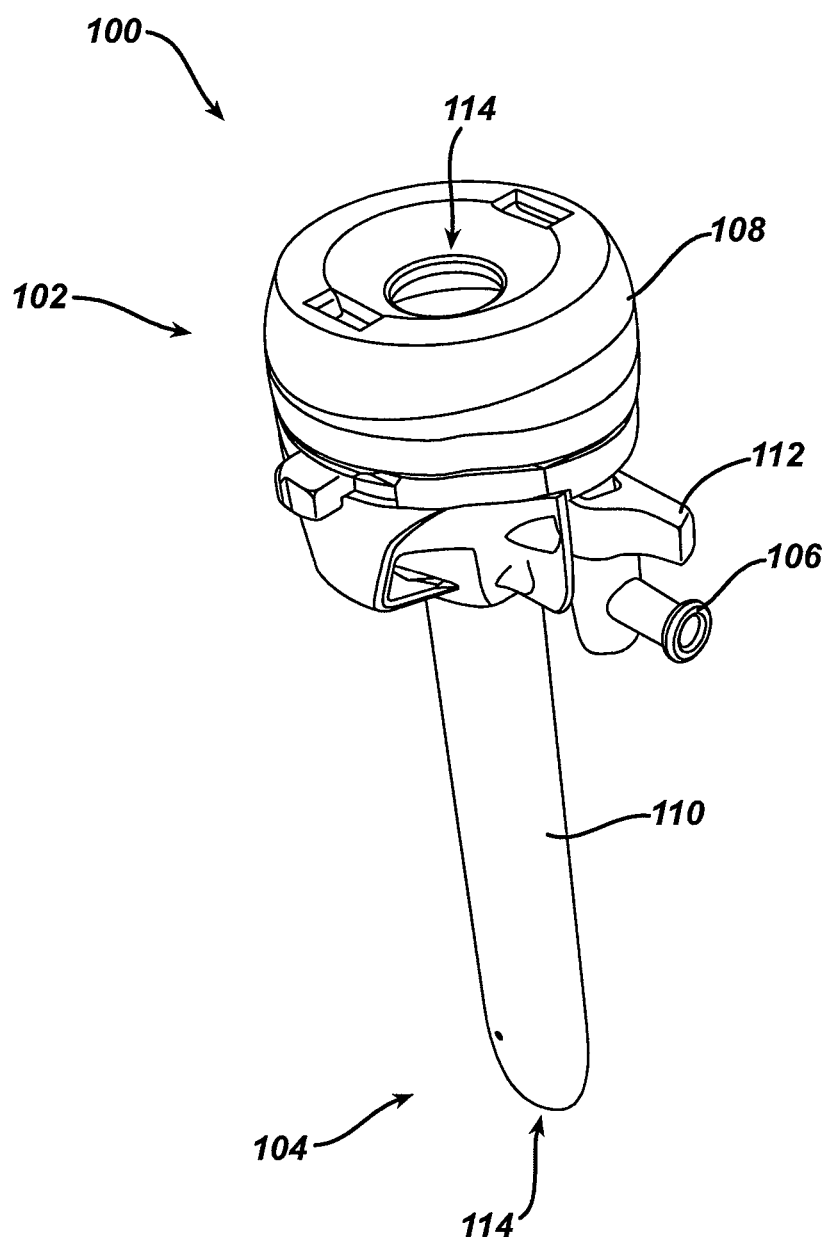
FIG. 1 is a perspective view of one exemplary embodiment of a surgical access device having an body that defines a working channel configured to allow for passage of surgical instruments.

FIG. 1 illustrates one exemplary embodiment of a surgical access device 100. The surgical access device 100 can have a variety of configurations, but as shown, the surgical access device can be in the form of a trocar assembly. The surgical access device 100 generally can include a body with proximal 102 and distal ends 104, and the body can define a working channel 114. The working channel 114 can be adapted to pass surgical instruments therethrough, for example to access a surgical site. The body of the surgical access device 100 need not be uniform. For example, as shown in FIG. 1, the surgical access device 100 can include a housing 108 and a cannula 110 or hollow tube extending distally therefrom. The surgical access device 100 also can include an inlet 106 or insufflation port, which in many embodiments can receive a gas (such as carbon dioxide) which can be used for insufflation of a body cavity into which the surgical access device 100 is inserted, as is known in the art. In other embodiments a wide range of gases, including virtually any bio-compatible gas, can be used. A control element 112, here illustrated as a rotatable tab, can be coupled to the inlet 106 for controlling gas flow therethrough, for example via a valve element which can be disposed in the housing 108.

Figure 2:
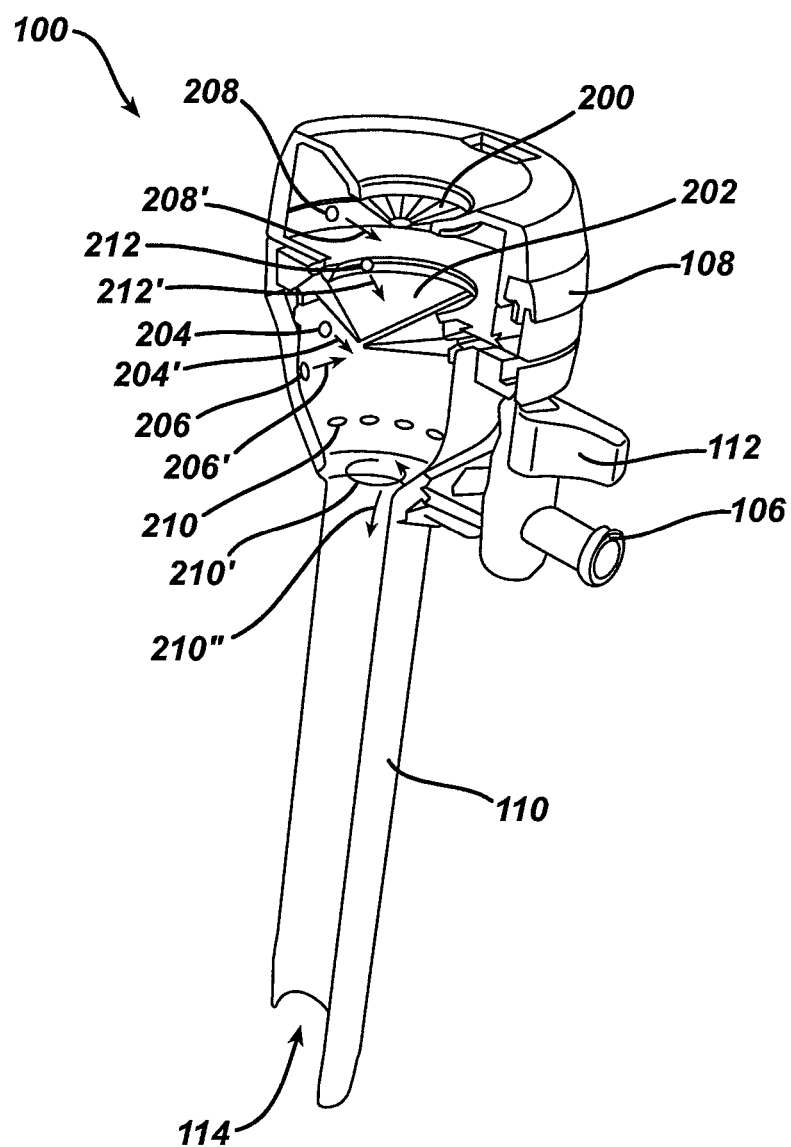
FIG. 2 is a sectioned perspective view of the surgical access device shown in FIG. 1 which shows a plurality of exemplary outlets for directing gas flow towards seals in the working channel.
Figure 3:
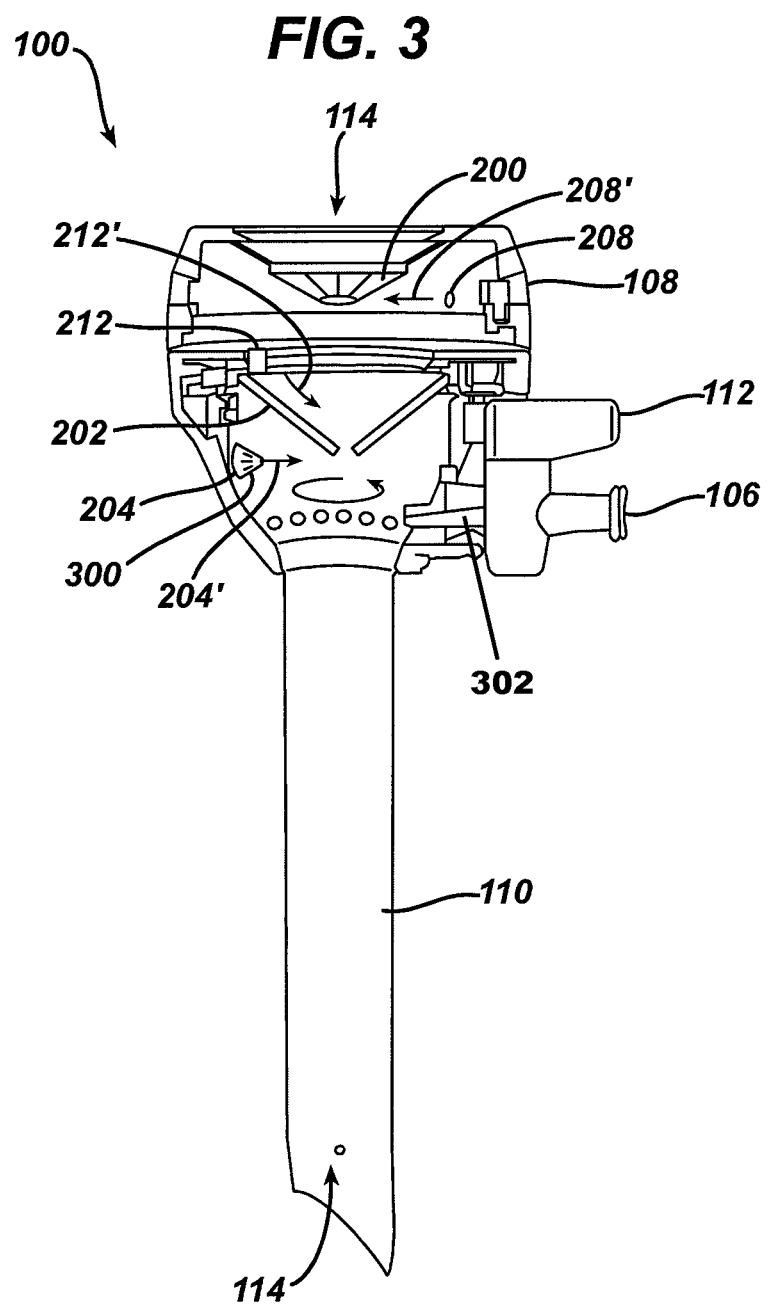
FIG. 3 is a sectioned side view of the surgical access device shown in FIG. 1 which shows a plurality of exemplary outlets for directing gas flow towards seals in the working channel.

FIGS. 2 and 3 illustrate further features of the surgical access device 100. For example, the surgical access device 100 can include one or more seals 200, 202, which can vary widely in form. The seals 200, 202 can be disposed at virtually any location in the working channel 114, and can extend at least partially across the working channel 114 so as to contact a surgical instrument passed therethrough and create a seal against the instrument. As shown in FIGS. 2 and 3, a wide variety of seals having a wide variety of shapes and sizes can be used. For example, as shown in the illustrated embodiment, the surgical access device 100 can include a proximal multi-layer seal 200 and a distal duckbill seal 202 or other seal having one or more slits formed therein. Such seals can extend to varying degrees across the working channel 114, as some may extend only slightly into the working channel 114, while others may completely span (or almost completely span) the distance across the working channel 114.

One or more outlets 204, 206, 208, 210, 212 (hereinafter collectively referred to as "outlets 204-212"), can open into the working channel 114. The outlets 204-212 can be disposed at various locations in the working channel 114. Further, the outlets 204-212 can have a variety of configurations and can be coupled to a variety of gas sources, as will be described in more detail below. However, in one embodiment, the outlets can be coupled to the inlet 106 via, for example, channels formed within the housing 108. The channels and outlets 204-212 can bring gas flow from the inlet 106 to the working channel 114 and can direct gas flow towards one or more of the seals 200, 202. Although gas flow can be directed in a wide variety of ways, in the illustrated embodiment of FIG. 2, exemplary gas flow from the outlets 204-212 is illustrated by the arrows 204', 206', 208', 210', 212' (hereinafter collectively referred to as "arrows 204'-212'"). Depending on the orientation of such outlets and the nature of the gas flow (for example the pressure/velocity), gas flow can be directed against, across, or around the seals, in a parallel or tangential fashion relative to the seals, or in virtually any desired fashion. In use, such gas flow can remove fluid from the seals 200, 202 (or from wherever the gas flow is directed) and can prevent accumulation of fluid. Such gas flow can also remove fluid from instruments. For example, gas flow can blow off fluid on the lens and/or shaft of a scope as it is retracted or inserted through the working channel 114, preventing or reducing the opportunity for such fluid to be transferred to the seals 200, 202 or other part of the surgical access device 100.

Referring to FIGS. 1-3, the surgical access device 100 can have a wide variety of shapes and sizes, and can be made of virtually any bio-compatible material, for example, plastic. As previously mentioned, in some embodiments, the surgical access device 100 can have an body (in some cases, an elongate body) with a working channel 114 defined therethrough. Both the body and working channel 114 can be of any width or diameter. The working channel 114 can have circular, oblong, or any other cross-sectional shape, and can be of any width (or diameter) along part or all of its length. In some embodiments, the working channel can have a width or diameter between about 3 and about 30 mm. However, it should be understood that the size of the working channel 114 need not be uniform along its length, as shown in FIGS. 2-3.

As previously mentioned, the surgical access device 100 can include a housing 108 and cannula 110, which can have a wide variety of forms. The housing 108 can be of virtually any shape and size. In some embodiments, the housing 108 can be ergonomically shaped and sized to facilitate user-manipulation (for example, to facilitate twisting the surgical access device with an obdurator extending therethrough for entering a body, or to facilitate manually orienting the surgical access device 100 to adjust a view of a scope extending through the surgical access device 100 into a body). In some embodiments, the cannula 110 can have surface features 520, such as ridges (best seen in FIG. 5), formed thereon to reduce slippage in circumstances where the surgical access device 100 is seated through the skin. The distal end 104 of the cannula 110 can be tapered or pointed, as shown in FIGS. 1-3. It should be understood that the surgical access device 100 can be a trocar of any kind, including bladeless, blunt tip, and dilating trocars. More information about surgical access device, including trocars, can be obtained from U.S. patent application Ser. No. 11/855,777, titled "Trocar Assembly" and filed Sep. 14, 2007, and Ser. No. 11/781,645, titled "Surgical Access Device" and filed Jul. 23, 2007, the teachings of which are hereby incorporated by reference in their entireties.

Figure 4A:
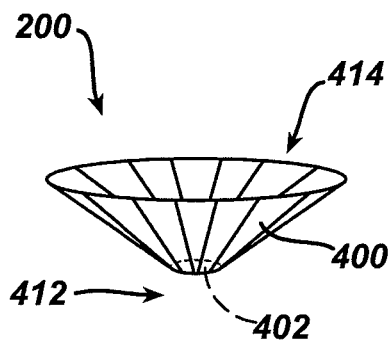
FIG. 4A is a perspective view of an exemplary seal and illustrates exemplary gas flows that can be directed at the seal for removing fluid therefrom.
Figure 4B:
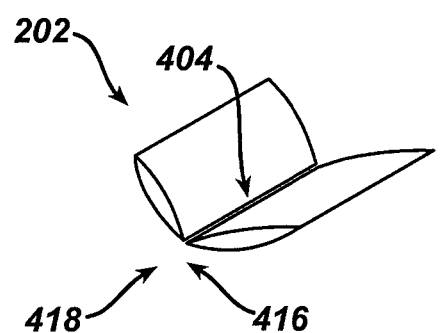
FIG. 4B is a perspective view of another exemplary seal and illustrates exemplary gas flows that can be directed at the seal for removing fluid therefrom.
Figure 4C:
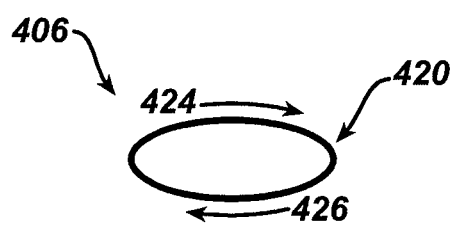
FIG. 4C is a perspective view of yet another exemplary seal and illustrates exemplary gas flows that can be directed at the seal for removing fluid therefrom.
Figure 4D:
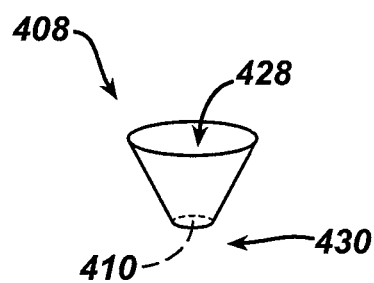
FIG. 4D is a perspective view of yet another exemplary seal and illustrates exemplary gas flows that can be directed at the seal for removing fluid therefrom.

Any kind of seal can be used in the surgical access device 100. As shown in FIGS. 2-3 and with more detail in FIG. 4A, seal 200 can be a multi-layer seal. Such a multi-layer seal 200 can include a plurality of flaps 400 disposed around a central opening 402. As shown in FIGS. 2-3 and with more detail in FIG. 4B, seal 202 can have an opening 404 formed therein which can be generally slit-shaped, and further can be configured as a duckbill seal as is known in the art. The opening 404 can be narrow and linear in some embodiments, while in others it can be non-linear (for example, a curved, sawtooth or zig-zag pattern). FIGS. 4C and 4D illustrate other exemplary seals, along with arrows indicating exemplary gas flows that can be directed towards such seals. FIG. 4C shows an exemplary seal 406 which is the in the form of an O-ring. The O-ring can be of any shape and size, for example, the O-ring can be circular in cross section or can be rectangular and/or shaped like a bushing. FIG. 4D shows an exemplary funnel-shaped seal 408 which includes a central opening 410. Other possible seals include flapper seals, annular seals, a zero-closure seals (including zero-closure multi-layer seals), universal seals, diaphragms, O-rings, and gel seals.

In some embodiments, different seals in the surgical access device 100 can be adapted for different purposes. For example, in FIGS. 2-3, multi-layer seal 200 can be adapted to contact a surgical instrument when it is disposed in the working channel 114, while seal 202 can be adapted to create a seal when no instrument is disposed in the working channel 114. However, in some embodiments, the seals need not be configured to contact and/or seal against a surgical instrument. For example, seals can be provided to impede insufflation gas flow and/or to prevent objects of certain sizes from passing therethrough.

In many cases, the seals can be made of an elastomeric material such as rubber. However, any bio-compatible material can be used, including many kinds of plastics. Further information about seals can be obtained from U.S. Pat. Nos. 5,628,732; 5,792,113; and 5,350,364; and U.S. patent application Ser. No. 11/952,464, titled "Trocar Seal With Reduced Contact Area" and filed Dec. 7, 2007, the teachings of which are hereby incorporated by reference in their entireties. FIGS. 4A-D also include arrows 412 to 430 which illustrate exemplary gas flows which can be directed towards the seals, as will be discussed in more detail below.

The outlets 204-212 can have a wide variety of configurations. For example, the outlets 204-212 can be circular, oblong, rectangular and so on. In some embodiments, the outlets 204-212 can take the form of openings formed in the working channel. Such openings may be of any shape and size, for example in some embodiment one or more outlets can be narrow openings or slits formed in the working channel 114. In some embodiments, the outlets 204-212 can be flush or recessed from an interior wall of the working channel, while in other embodiments the outlets 204-212 can protrude or extend from an interior wall of the working channel. However, it can be advantageous to configure the outlets so as to avoid interfering with a surgical instrument in the working channel 114. Further, nozzles can be coupled to the outlets or formed on the outlets to direct gas flow therethrough and/or to create desired the desired flow of gas towards a seal. An exemplary tapered nozzle 300 is illustrated in FIG. 3 coupled to outlet 204. Outlets and nozzles can be oriented to direct streams of gas at a seal in flows that are suitable for removing fluid.

Arrows 204'-212' shown in FIGS. 2-3 illustrate exemplary gas flows from the outlets 204-212 towards one or more seals in the surgical access device 100. For example, arrow 204' indicates that outlet 204 can direct gas across a linear opening formed in seal 202. Arrow 206' indicates that outlet 206 can direct gas along or parallel to the linear opening formed in seal 202. Arrow 208' indicates that outlet 208 can direct gas across a central opening in seal 200. Arrow 210' indicates that outlets 210 can direct gas in an annular fashion around the working channel 114 at a point distal to seal 202. Arrow 210" indicates that outlets 210 can direct gas downward into the working channel 114 in cannula 110. In other embodiments, outlets 210 can direct gas across the working channel 114 to form a gas curtain (or in other words, a shield formed by flowing gas). A gas curtain can be created, for example, with a continuous flow of gas that is suitable to prevent or impede fluid from passing and thereby prevent/reduce its accumulation on the seal (or other surface) behind the gas curtain. An outlet can be disposed proximal to seal 200 or seal 202 to form such a gas curtain across the working channel 114. Arrow 212' indicates that outlet 212 can direct gas downwards onto or against seal 202.

FIGS. 4A to 4D include arrows to illustrate yet other exemplary gas flows that can be directed towards seals from outlets. Arrow 412 indicates that gas can be directed across a central opening of seal 200, while arrow 414 indicates that gas can be directed onto or against seal 200. Arrows 416 and 418 indicate that gas can be directed perpendicular to and parallel to opening 404 of seal 202, respectively. Gas flows can also be directed against opening 404. Arrows 424 and 426 indicate that gas can be directed around O-ring seal 406, while arrow 420 indicates that gas can be directed against seal 406. Arrow 428 indicates that gas can be directed down onto seal 408 and against an opening 410 therein. Arrow 430 indicates that gas can be directed across opening 410 of the seal 408.

Additionally, several outlets can be located in conjunction with one another such that, collectively, they produce a desired flow. For example, multiple outlets can be oriented in a directional ring around the inside perimeter of the working channel 114 to create an annular gas flow. Alternatively, circular or annular gas flow can be created with an outlet formed by a opening or slit formed at least partially around the inner periphery the working channel 114, such as an annular opening.

It should be understood that the outlets 204-212 shown in FIGS. 1-3 illustrate exemplary locations for the outlets 204-212 and that the number and location of such outlets can vary widely. Any configuration which removes fluid or which prevents fluid from accumulating can be used. In many embodiments, the configuration of the outlets can depend on the location, shape and size of the seals in the working channel 114.

As previously mentioned, the outlets 204-212 can be coupled to the inlet 106 via one or more internal channels or tubes formed in the housing 108. The internal channels, such as internal channel 302 shown in FIG. 3, can distribute gas from the inlet 106 to the various outlets 204-212. In some embodiments all outlets can be coupled to an inlet that is for insufflation purposes. However, in other embodiments, one or more dedicated fluid-removal inlets can be provided so as to segregate gas distribution for insufflation and removal of fluid. Such a configuration can accommodate for differences between gas for insufflation and fluid-cleaning. For example, different gases, pressures, and flow characteristics (for example, continuous vs. periodic flow) can be used for insufflation vs. fluid-cleaning. In some embodiments, different outlets can be connected to separate inlets so that there can be such differences among the outlets used for fluid-cleaning (for example, outlets at different pressures, or some outlets providing continuous gas flow while others are periodic).

FIG. 5 shows an alternate embodiment of a surgical access device 500 in which inlets 404, 406, 408, 412 (hereinafter referred to collectively as "inlets 404-412") are included. Although any combination of connections is possible, each inlet 404-412 can be coupled to one or more outlets that are shown in FIG. 3. For example, inlet 404 can be coupled to outlet 204, inlet 406 can be coupled to outlet 206, inlet 408 can be coupled to outlet 208, inlet 412 can be coupled to outlet 212. Additional inlets can be included.

Figure 6:
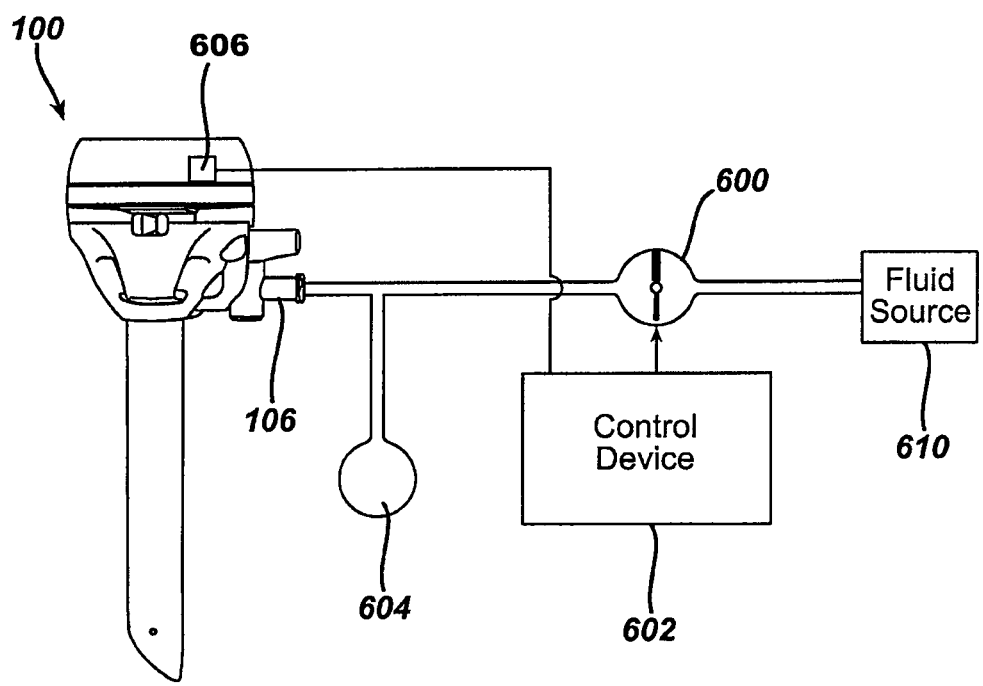
FIG. 6 is a schematic view of the surgical access device shown in FIG. 1 coupled to a valve element which is controlled by a control device, and further shows a sensing device coupled to the control device.

Valve elements can be included in the channels or otherwise associated with one or more outlets to control the gas flow therefrom. FIG. 6 shows a schematic view of an exemplary valve element 600 coupled to an inlet of surgical access device 100 to control gas flow from a gas source 610. Any number of such valve elements can be placed in a gas path to control gas flow to outlets collectively or independently. The valve elements can be disposed internally or externally to the surgical access device 100. It should be understood that the valve element 600 can be in addition to the control element 112 that was illustrated in FIG. 1 (and was described as a rotatable tab coupled to inlet 106), or can be provided for inlets that do not have a control element 112.

Although the valve element 600 in FIG. 6 is illustrated with a rotating flap, any kind of valve element can be used. The valve element 600 can be coupled to a control device 602, such as lever, button, foot pedal, or other actuator, which can allow a user to actuate the valve element 600 and thereby control the flow of gas to one or more of the outlets. Also, in some embodiments, a user-actuated pumping device 604 can be coupled to one or more of the outlets. For example, a hand-actuated bulb can be provided, and can allow a user to manually initiate a jet of gas.

The control device 602 can include an electronic system, or can be coupled to one. Such a configuration can provide for automated fluid-cleaning at predetermined times or intervals. The control device 602 can also be coupled to a sensing device 606 to determine when to clear fluid. For example, a pressure sensor or pressure-actuated switch in the surgical access device 100 can sense when an instrument is inserted or retracted therethrough and can cause the control device 602 to trigger a jet of gas.

Figure 7A:
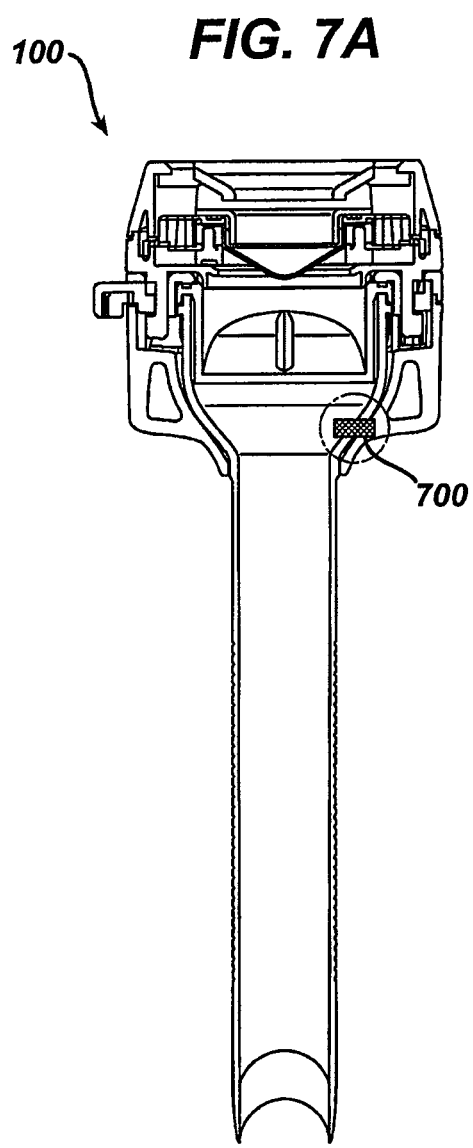
FIG. 7A is a sectioned side view of the surgical access device shown in FIG. 1 with an exemplary exhaust port formed therein.
Figure 7B:
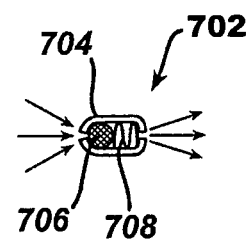
FIG. 7B is a schematic view of one embodiment of an exhaust port for the surgical access device shown in FIG. 7A.
Figure 7C:
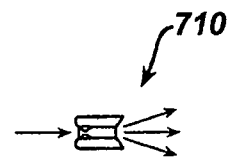
FIG. 7C is a schematic view of another embodiment of an exhaust port for the surgical access device shown in FIG. 7A.

FIG. 7A shows an exemplary exhaust port 700 which can be included in the surgical access device 100. Exhaust port 700 can be configured to release or vent excess gas within the working channel 114. Exhaust port 700 can have a wide variety of forms. As shown in FIG. 7B, the exhaust port 700 can be a constant pressure relief valve 702. Relief valve 702 can include a housing 704 which includes a stopper element, such as a ball 706, that is disposed against a biasing element, such as a spring 708. The stopper element, biasing element, and other characteristics of the valve 702 can be configured to release gas from the working channel 114 once it reaches a selected level. The exhaust port 700 can also be in the form of a calibrated mass flow orifice 710, as shown in FIG. 7C. The calibrated mass flow orifice 710 can be made of ceramic, metal, plastic, or any other bio-compatible material. Exhaust port 700 also can be coupled to a control device to receive input from a user or from a sensing device, to determine when and how much gas to release.

In use, inlet 106 (or other inlets, as previously mentioned) can be coupled to a gas source, and gas can be directed periodically or continuously towards one or more of the seals 200, 202 (in any fashion previously described, for example). Any kind of gas can be used, although in some embodiments it can be convenient to use carbon dioxide if it is already available for insufflation purposes. In some embodiments, a vapor or a cleaning fluid can be introduced through the outlets, optionally followed by suctioning. In yet other embodiments, suctioning can be provided through the outlets. Gas flow can remove fluid accumulated on a seal during a surgical procedure and prevent its transfer to a surgical instrument, such as a laparoscope or endoscope, which is being passed through the working channel 114. Gas flow also can remove fluid on a surgical instrument as it is moved through the working channel, preventing or reducing the opportunity for such fluid to be transferred onto the seals or other parts of the surgical access device. Typically, such surgical instruments are passed through the working channel 114 to a surgical site at the distal end 104 of the surgical access device 100. Gas flow can also have the effect of removing fluid from surgical instruments themselves as they are inserted into or removed from the working channel 114. For example, gas flow directed towards seals can have such an effect. Further, gas flow can be directed into the working channel 114, but not necessarily towards a seal, to create a gas curtain which can remove fluid from a surgical instrument as it passes therethrough, and/or prevent fluid from passing the curtain into the surgical access device 100. Gas flow can be at any pressure suitable for removing fluid or preventing/reducing its accumulation. In some embodiments, the pressure ranges can be suitable for laparoscopy. By way of non-limiting example, gas can be pressurized in a range of about 14 to 22 mmHg.

Figure 8:
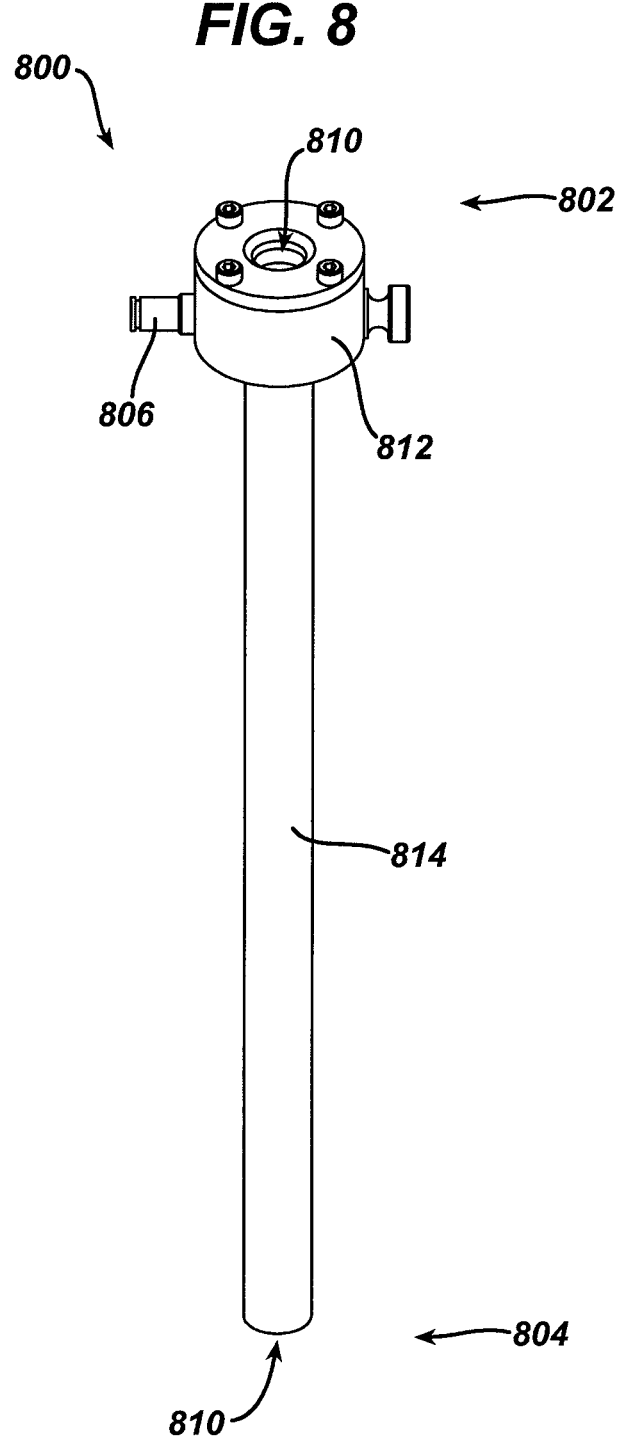
FIG. 8 is a perspective view of an exemplary sleeve for receiving a surgical instrument and creating a gas curtain across a portion of the surgical instrument.
Figure 9:
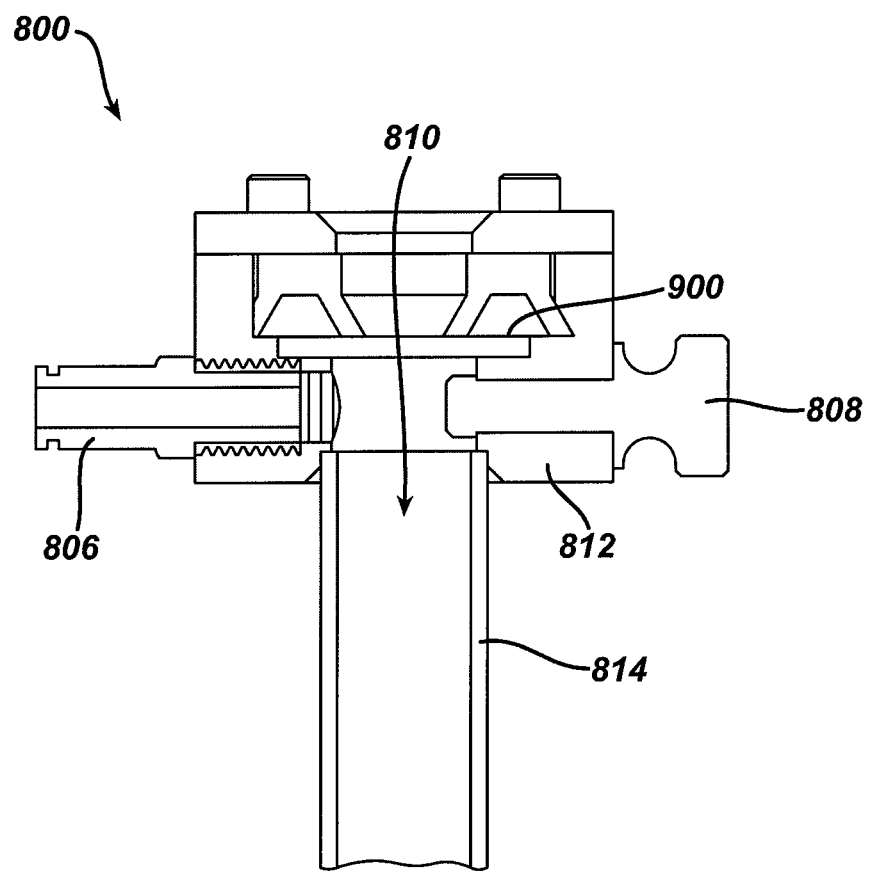
FIG. 9 is a sectioned side view of the proximal end of the sleeve shown in FIG. 8.

FIG. 8 illustrates one exemplary embodiment of a sleeve 800 which can be useful for cleaning fluid from a surgical instrument and/or for reducing the accumulation of fluid on a surgical instrument. As shown, the sleeve 800 can include a body with proximal and distal ends 802, 804. The body can define a working channel 810, which can be shaped and sized to receive a surgical instrument, such as a laparoscope or endoscope. The body can include a housing 812 with tube 814 extending distally therefrom. The housing 812 can include a port 806 for receiving gas into the working channel 810, as shown in more detail in FIG. 9. The housing also can include a screw 808, which can extend into the working channel 810 and which can be tightened against a surgical instrument inserted into the sleeve 800. A grommet (such as an elastomeric O-ring) can be disposed around the working channel 810 to form a seal against a surgical instrument inserted therein.

Figure 10:
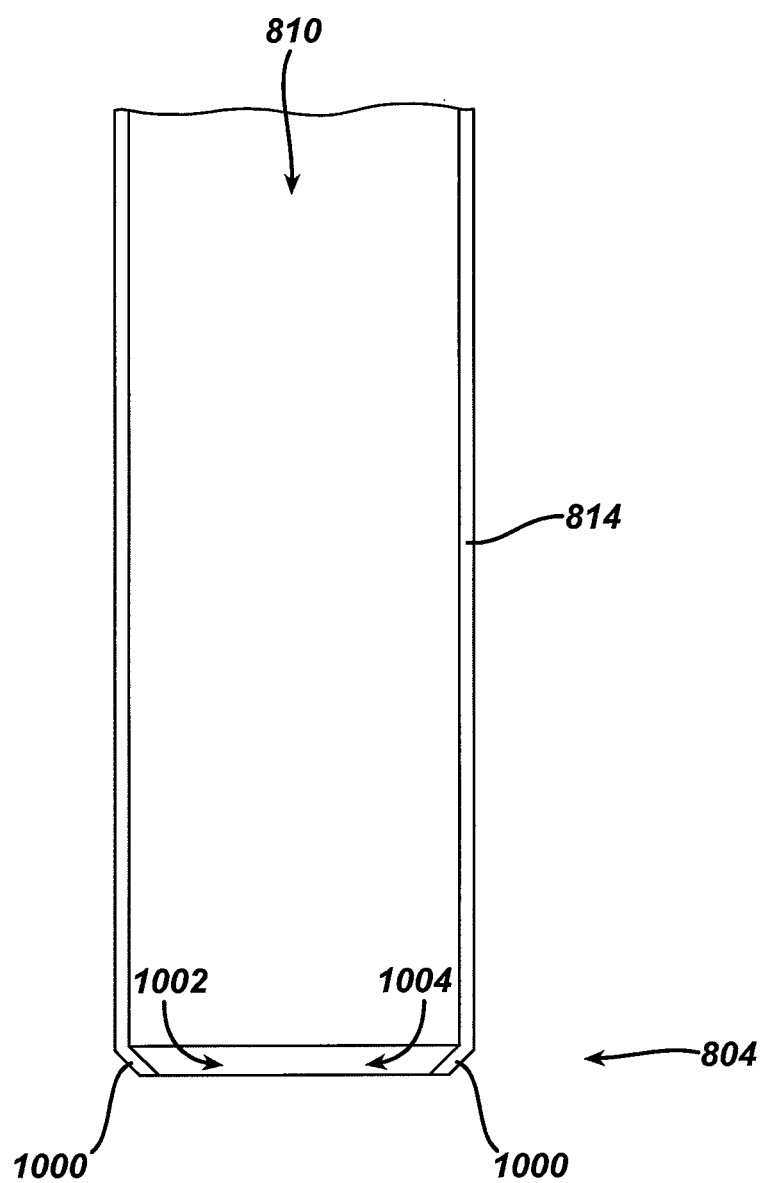
FIG. 10 is a sectioned side view of the distal end of the sleeve shown in FIG. 8.

As shown in FIG. 10, the distal end 804 of the tube 814 can be beveled. Bevel 1000 can be shaped to direct gas laterally across the working channel 810, as shown by exemplary arrows 1002, 1004. In many embodiments, the sleeve 800 can be sized such that when fully inserted the distal end of the surgical instrument is disposed near or at the beveled distal end 804 of the tube 814. In some embodiments, the sleeve 800 can include a size adjuster (such as a threaded cylinder which can be rotated to extend proximally from the housing 812 in a progressive manner), which can allow one to adjust the length of the working channel 810 and thereby bring the distal end of an inserted surgical instrument in proximity to the beveled distal end 804.

In use, a surgical instrument can be inserted into the working channel 810 of the sleeve 800. If desired or necessary, the distal end of the instrument can be brought in proximity to the distal end 804 of the sleeve 800. The screw 808 can be used to lock the surgical instrument in place. Gas can be directed through the port 806, distally through the working channel 810, and across the distal end or face of the surgical instrument via bevel 1000. In some embodiments, a continuous or substantially continuous flow of gas can be directed to the distal end 804 of the tube 814, across the working channel 810, and across the distal end or the distal face of a surgical instrument. Such a continuous flow of gas can create a gas curtain, which can reduce/prevent fluid from accumulating on the distal end of a surgical instrument. For example, such a curtain, which can be created by a boundary layer of flowing gas, can help to keep the lens of a scope clear of fluid, thus enhancing visualization. Fluid approaching the gas curtain can be deflected, and fluid adhering to the surgical instrument can be removed by the constant flow. The surgical instrument, with the sleeve 800 attached, can be inserted and removed from a surgical site, for example through a natural orifice or via a trocar with reduced fluid accumulation.

A range of variations are possible. For example, in other embodiments, the port 806 can be coupled to a channel formed in or along the working channel, so that gas flow for fluid-removal purposes is separated from the working channel 810 as it is delivered to the distal end of the tube 814. In other embodiments, gas flow can be controlled by a valve mechanism, control device and/or sensing device, as previously described in connection with FIG. 6. Further, as one skilled in the art will understand, a variety of gases, cleaning agents and/or fluids, can be used.

Figure 11:
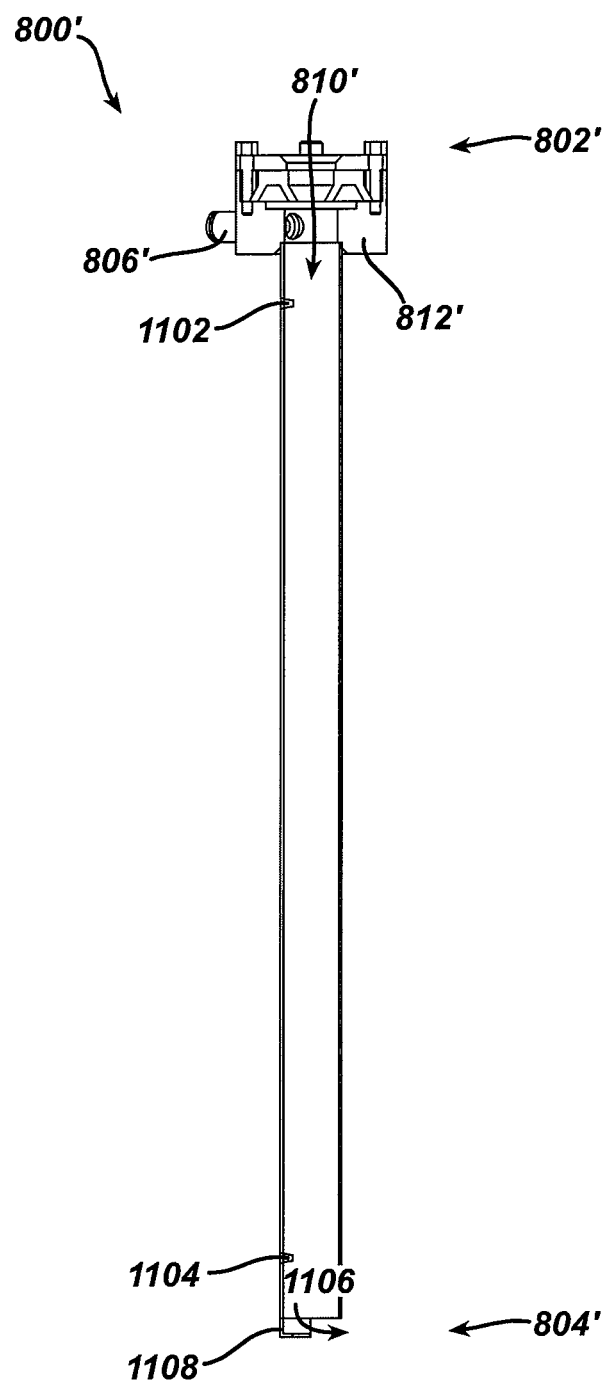
FIG. 11 is a sectioned side view of an alternate embodiment of a sleeve for receiving a surgical instrument which includes a diverter at a distal end thereof, and, FIG. 12 is a perspective view of the distal end of the sleeve shown in FIG. 11.
Figure 12:
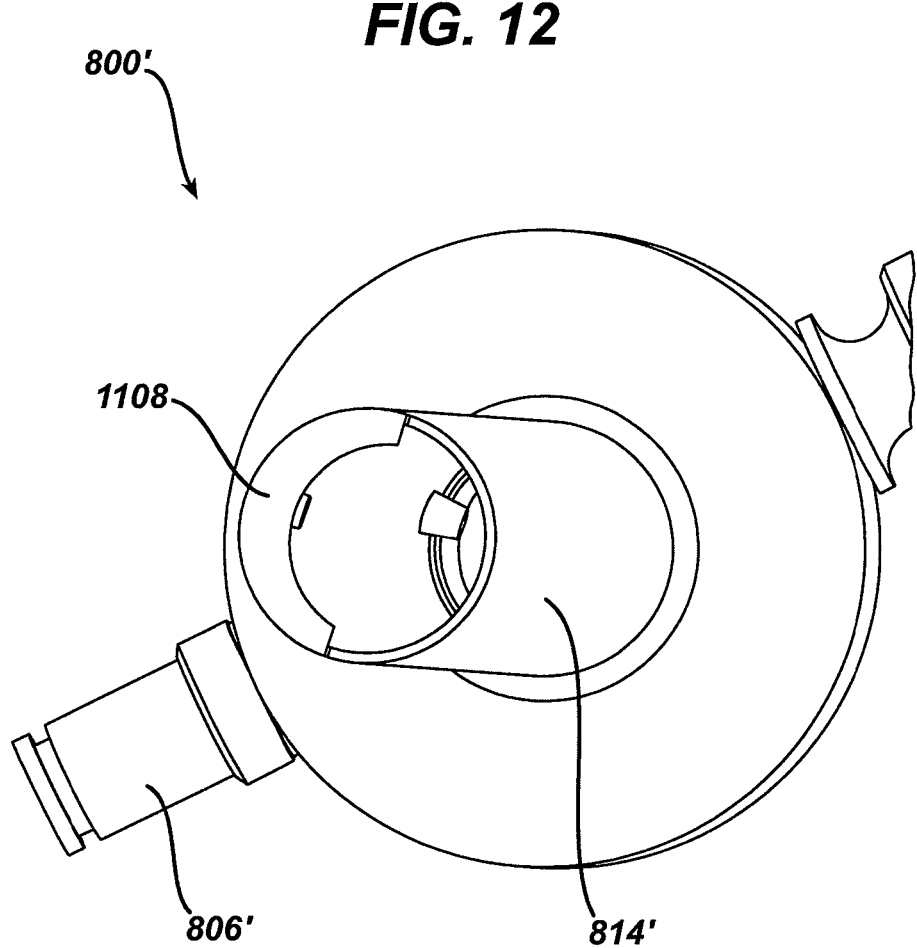

FIG. 11 illustrates an alternate embodiment of a sleeve 800' for a surgical instrument. As shown, sleeve 800' can have a diverter 1108 at a distal end 804' thereof. Spacers 1102 and 1104 can be included in the working channel 810' to align the surgical instrument, and/or maintain the surgical instrument at a fixed distance from the inner wall of the working channel 810' to allow for gas flow to the distal end 802', and also can provide appropriate spacing for proper function of the diverter 1108. Arrow 1106 illustrates exemplary gas flow out of the diverter 1108 and across a distal end 804' of the sleeve 800'. FIG. 12 illustrates a more detailed view of the diverter 1108. The diverter can have a variety of shapes, including any shape sufficient to direct gas across an end of the surgical instrument. However, as shown the diverter 1108 has a substantially crescent shape and extends approximately halfway around the circumference of the distal opening of the working channel 810'.

The sleeves described above in connection with FIGS. 8-11 can be employed as an accessory or a retrofit to a surgical instrument. For example, a sleeve can be used an overtube for a surgical instrument such as a scope, and the scope assembly with the overtube can be inserted through a surgical access device, such as a trocar. Alternatively, the features of the sleeves described above can be integrated into a surgical access device. For example, the features described above can be incorporated into a trocar.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning and/or replacement, and reassembly. Use of such techniques, and the resulting reconditioned device, are all within the scope of the present application.

Preferably, the devices described herein will be processed before surgery. First, a new or used tool is obtained and if necessary cleaned. The tool can then be sterilized. In one sterilization technique, the tool is placed in a closed and sealed container, such as a plastic or TYVEK bag. The container and tool are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility. It is preferred that the device is sterilized. This can be done by any number of ways known to those skilled in the art including beta or gamma radiation, ethylene oxide, or steam.

One skilled in the art will appreciate further features and advantages based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical access device, comprising:
a body defining a working channel configured and sized to allow for passage of a surgical instrument therethrough, wherein the body has a proximal housing and a distal cannula;
a seal extending across the working channel so as to contact a surgical instrument inserted therethrough;
at least one inlet formed through a sidewall of the proximal housing and configured to receive gas flow from an insufflation port; and
a plurality of outlets formed through an internal sidewall of the proximal housing at a location distal to the seal, the plurality of outlets being configured to receive gas flow from the inlet through at least one internal channel separate from the working channel and extending between the at least one inlet and the plurality of outlets and to deliver gas flow to the working channel, the plurality of outlets being oriented to direct gas flow towards the seal in the working channel for removing fluid on the seal, and the plurality of outlets being positioned a distance from a central longitudinal axis of the working channel, the distance being greater than a maximum radius of the cannula.

2. The surgical access device of claim 1, wherein the body includes a proximal housing and a distal cannula extending from the housing and configured to be inserted into a body cavity.

3. The surgical access device of claim 2, wherein the seal and the plurality of outlets are disposed in the proximal housing.

4. The surgical access device of claim 1, wherein the seal is at least one of a multi-layer seal, a duckbill seal, a flapper seal, an annular seal, a zero-closure seal, a seal with a slit-shaped opening, a universal seal, an O-ring, a diaphragm seal, and a gel seal.

5. The surgical access device of claim 1, wherein the plurality of outlets have tapered nozzles to focus gas flowing therefrom towards the seal.

6. The surgical access device of claim 1, wherein the seal has an opening formed therein and the plurality of outlets are oriented so as to direct gas toward the opening.

7. The surgical access device of claim 1, wherein the seal has a slit-shaped opening formed therein, and the plurality of outlets are configured to direct gas in one of a substantially perpendicular or parallel direction to the opening.

8. The surgical access device of claim 1, further comprising a valve element associated with the plurality of outlets to control gas flow therethrough.

9. The surgical access device of claim 8, wherein the valve element is coupled to a control device that provides signals to control gas flow through the valve element.

10. The surgical access device of claim 1, further comprising an exhaust port coupled to at least one of the working channel and the plurality of outlets.

11. The surgical access device of claim 1, wherein the plurality of outlets are oriented to direct gas flow against, across, or around the seal in the working channel.

12. The surgical access device of claim 1, wherein the plurality of outlets are disposed circumferentially around the seal in the working channel.

13. A surgical access device, comprising:
a body having a proximal end and a distal end and defining a working channel configured and sized to allow for passage of a surgical instrument therethrough;
a valve extending at least partially across the working channel and configured to form a seal across the working channel when no instrument is disposed therethrough;
a seal extending at least partially across the working channel and configured to contact and form a seal around a surgical instrument inserted therethrough;
an inlet extending into an outer sidewall of the body; and
a plurality of outlets formed in an internal sidewall of the body distal to the seal and configured to receive gas flow delivered into the inlet through at least one internal channel separate from the working channel and extending between the at least one inlet and the plurality of outlets, the plurality of outlets being oriented in a proximal direction to direct gas flow proximally towards the seal in the working channel for removing fluid on the seal.

14. The surgical access device of claim 13, wherein the plurality of outlets are oriented to direct gas flow against, across, or around the seal in the working channel.

15. The surgical access device of claim 13, wherein the plurality of outlets are disposed circumferentially around the seal in the working channel.

* * * * *